United States Patent
Henley

[11] Patent Number: 5,534,023
[45] Date of Patent: Jul. 9, 1996

[54] FLUID FILLED PROSTHESIS EXCLUDING GAS-FILLED BEADS

[76] Inventor: Julian L. Henley, 330 Orchard St., New Haven, Conn. 06511-4417

[21] Appl. No.: 225,507

[22] Filed: Apr. 11, 1994

Related U.S. Application Data

[63] Continuation of Ser. No. 998,530, Dec. 29, 1992, abandoned.

[51] Int. Cl.⁶ ........................................... A61F 2/12
[52] U.S. Cl. .................... 623/8; 623/7; 623/11; 623/66
[58] Field of Search ................. 623/7, 8, 11, 66

[56] References Cited

U.S. PATENT DOCUMENTS

| | | | |
|---|---|---|---|
| 2,542,619 | 2/1951 | Bernhardt | 623/7 |
| 3,845,507 | 11/1974 | Kirby et al. | 623/7 |
| 3,852,833 | 12/1974 | Koneke et al. | 623/7 |
| 4,651,717 | 3/1987 | Jakubczak | 623/8 |
| 4,701,230 | 10/1987 | Loi | 623/7 |
| 4,963,150 | 10/1990 | Brauman | 623/8 |
| 4,969,898 | 11/1990 | Calogero | 623/7 |
| 5,007,929 | 4/1991 | Quaid | 623/8 |
| 5,074,878 | 12/1991 | Bark et al. | 623/8 |
| 5,236,454 | 8/1993 | Miller | 623/8 |

FOREIGN PATENT DOCUMENTS

| | | | |
|---|---|---|---|
| 0322194 | 6/1989 | European Pat. Off. | 623/8 |
| 792692 | 4/1958 | United Kingdom | 623/7 |
| 858878 | 1/1961 | United Kingdom | 623/7 |
| 1110479 | 4/1968 | United Kingdom | 623/7 |

*Primary Examiner*—Paul B. Prebilic
*Attorney, Agent, or Firm*—Michael G. Petit

[57] ABSTRACT

An implantable prosthetic device having a biocompatible elastomeric shell and a polyphasic filler material consisting of gas-filled chambers or beads bathed in a biocompatible fluid. In a preferred embodiment the solid and gaseous phases of the filler comprise interconnecting flexible chains of small gas-filled beads. The gas-filled beads may be continuously extruded in a chain with a fiber of extrudate connecting the beads. In one embodiment, the extruded chains of beads are formed into a mass having the desired shape of the prostheses where they may be further crosslinked, then placed within an outer shell. The void space between the beads is filled with a biocompatible fluid such as saline. The polyphasic filler preferably has a density which is less than or equal to the density of the surrounding tissue thereby reducing microtrauma to the capsule associated tissue and the incidence and/or severity of capsular contracture. The prosthesis does not collapse, wrinkle or otherwise become deformed during use; even in the case of rupture. In another embodiment, gas-filled beads are injected endoscopically into a previously placed, fluid-filled implant to displace the liquid filler and alter the density of the filler. The effective density of the polyphasic filler can be adjusted by varying the ratio of the volume of encapsulated gas to the weight of the encapsulating solid phase.

2 Claims, 2 Drawing Sheets

FLUID FILLED PROSTHESIS EXCLUDING GAS-FILLED BEADS

CROSS REFERENCE TO RELATED APPLICATIONS

This application is a continuation of Ser. No. 07/998,530 filed Dec. 29,1992 now abandoned.

BACKGROUND OF THE INVENTION

1. Field of the Invention

This invention relates to fluid-filled prosthetic implants and more particularly to filling materials for medical implants.

2. Prior Art

Medical grade Silastic® brand of silicone elastomer has a long established record of safety and bio-compatibility with clinical data extending back nearly 35 years. Numerous implantable medical products, including implantable post-cataract eye lenses, heart valves, and other devices are made from this material. Over the past 30 years the outer shells of fluid or foam-filled implantable breast prostheses have been made from silicone elastomer and such prostheses are widely used for breast reconstruction following surgical mastectomy and augmentation of hypo-plastic breast tissue.

Extensive clinical data supporting the safety of silicone elastomer for implantation has been established. Recently, it has been suggested that implanted prosthetic devices comprising an elastomeric shell enclosing a silicone gel may lead to clinical problems, most of which are putatively related to the migration of the liquid silicone gel filler through the shell into the surrounding tissue. The U.S. Food and Drug Administration (FDA) has recently restricted the use of such silicone gel-filled implants to reconstructive applications and limited silicone gel augmentations to patients subject to FDA supervision. The reason for the recent action of part of the FDA has been the uncertainty surrounding the safety of gel-filled silicone implants for breast augmentation and reconstruction. Many patients have received such implants over the past 30 years and are now experiencing anxiety regarding the safety of their existing prosthesis. Furthermore, since silicone gel is radiopaque, it may interfere with x-ray detection of tumors.

New non-gel-filled versions of such prostheses, usually saline filled, are currently available and have been for some time. Saline has the advantage of being more radiolucent than silicone gel. Some of these prostheses employ an impermeable barrier for a shell material or to underlie the shell to minimize the migration of filling fluid from the prosthesis. Shells are now also commonly textured to facilitate the ingrowth of tissue and to reduce capsular contracture and anchor the prosthesis. Existing saline-filled prostheses, although meeting FDA safety and efficacy requirements, suffer from the difficulty that many of them rupture after implantation causing difficulty for the patient as the prosthesis collapses. In addition, while texturing the outer surface of the shell to reduce capsular contracture appears to be at least partially effective, many patients still experience such contracture following implantation. Further, since water and saline are denser than breast tissues, that is, they have a specific gravity greater than breast tissue, the weight of the filler displaces surrounding tissue and stretches the elastomeric shell causing cosmetically unacceptable wrinkling. Such surface wrinkling is believed to contribute to device failure by shell rupture and subsequent collapse. Over-inflation reduces this effect but contributes to spheralization and unnatural shape and feel.

Capsular contracture has received a great deal of attention in recent years. A capsule enclosing a foreign object implanted beneath the skin is a normal response. The capsule partitions the implanted object from the body. The formation of the capsule is, in itself, not usually a problem cosmetically. In many cases, however, for reasons that are still obscure, the capsule contracts, pulling itself into a hard spherical body which compresses the implanted prosthesis. Such spherical contracture is disfiguring and the capsule must be either ruptured or removed. The problem is discussed in U.S. Pat. Nos. 4,963,150 to Brauman and 4,889,744 to Quaid. It is generally believed that texturing the outer surface of a implantable prosthesis to permit tissue ingrowth disorients the collagen fibrils in the capsule thereby reducing capsular contracture. While it appears that an open-cell or textured surface reduces the incidence of capsule contracture, the mechanism for such a reduction is not known. It is desirable to provide an implantable fluid-filled prosthesis which does not utilize radiopaque silicone-gel yet retains its form and natural, tissue-like feel. It is also desirable that the prosthesis have viscoelastic properties that are similar to surrounding tissue and further reduce capsule contracture by reducing torque and mechanical forces at the prosthesis-tissue boundary.

SUMMARY OF THE INVENTION

It is an object of this invention to provide a fluid-filled medical implant that has a density less than or equal to breast tissue.

It is another object of this invention to provide polyphasic filler material for a medical implant having solid and gaseous phases which do not migrate in the case of rupture.

It is another object of this invention to provide a prosthesis for implantation which can be at least partially filled with relatively inelastic bio-compatible liquids, such as normal saline, dextran or hyaluronic acid and retain its shape.

It is another object of the invention to provide a fluid-filled prosthesis that will retain its structural shape, even in the event of a rupture of the outer shell.

It is yet another object of this invention to provide a means for regulating the density of the prosthesis while retaining the natural characteristics that are desirable of such prosthesis.

It is still another object of this invention to provide diphasic filler material that may be introduced transdermally into a previously implanted fluid-filled prosthesis to displace a portion of the fluid contained therein and reduce the effective density thereof.

Given the existing regulatory climate and uncertainty surrounding the safety of silicone gel-filled prostheses, such a prosthesis will obviate the current problems noted with silicone gel-filled implants and may also significantly reduce capsular contracture problems that have afflicted many prostheses for a number of years. Considering the number of patients presently having implants that are deemed unsafe by the FDA, it is critical that a fluid-filled prosthesis be provided which solves the problems identified above and does not require use of the silicone gel.

DESCRIPTION OF THE PREFERRED EMBODIMENTS

Before describing the various embodiments of the polyphasic filler material suitable for implantable prosthetic devices it will be helpful to digress for a moment and consider the viscoelastic coupling between an implanted breast prosthesis and the surrounding tissue as a possible factor in promoting capsular contracture. Although viscoelastic coupling may not be the primary factor in encapsulation, it may be an important factor in capsule contracture and the concurrent stiffening of the surrounding tissue. If a prosthesis has a different density and elastic behavior than the surrounding tissue, significant torsion and micro injury occurs at the interface between the surrounding tissue and the implanted prosthesis when the patient is in motion. A human body is more-or less constantly in motion, either by walking or other activity. During this activity, the momentum of the implanted prosthesis will cause displacement within its allotted space. Since the viscoelastic behavior as well as the density of the prosthesis is different than that of the surrounding fatty tissue, torsional and frictional effects occur; especially at the interface. These kinds of movements of the prosthesis (which can weigh anywhere from 200 to 800 grams and will experience translational excursions whether or not it is anchored and held rigidly to the chest wall) produces micro trauma resulting in minimal bleeding as well as tearing of small ingrowing blood vessels, at the capsule/tissue interface. This repetitive trauma at the capsule/tissue interface elicits a repetitive healing process. The repetitive healing of the torn tissue is accompanied by the migration of cells attempting to stabilize this prosthesis as well as heal the injury. This continued injury and healing process leads to contracture and hardening of the device, a common problem that afflicts as much as 5 to 40 percent of the patients receiving implanted breast prostheses. Encapsulation remains a natural process but often creates an undesirable result in breast implant surgery using currently available implants.

With the foregoing in mind, it is desirable that the implanted prosthesis have a density less than or closely approximating the density of the surrounding tissue so that the prosthesis and the surrounding tissue move together as a unit with minimum relative motion therebetween which can lead to tearing and micro-injury. Prior art silicone gel and saline-filled prostheses have a density greater than or equal to 1 g/cm$^3$, whereas the fatty tissue in the breast has a density in the order of 0.92 g/cm$^3$. If the repetitive trauma-healing-trauma scenario considered above is an important element contributing to spherical contracture of the capsule a density reduction of the prosthesis may significantly reduce the encapsulation and subsequent contracture.

Figure 1:
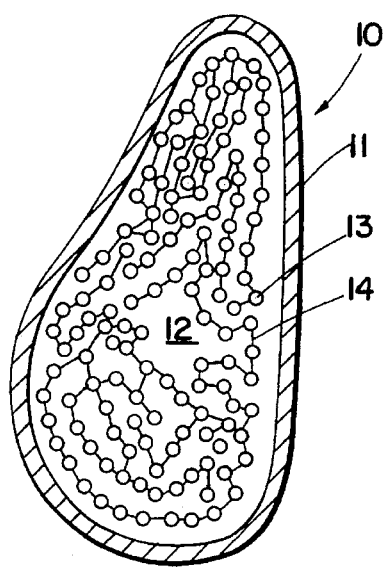
FIG. 1 is a cutaway section of a preferred embodiment of a fluid-filled prosthesis employing strings of interconnected beads or chambers to partially fill the interior of the prosthesis.

A preferred embodiment of the fluid-filled prosthesis of the present invention is shown in FIG. 1. The prosthesis 10 utilizes the existing technology of forming a shell 11 of silicone elastomer usually by dip-casting an elastomeric dispersion on a shaped mandril (not shown). According to current practice the shell is cured, peeled off the mandril and filled with a sponge or sealed with a patch and filled with a fluid according to methods well known in the art. The present invention teaches the incorporation of a polyphasic filler 12 comprising an interconnected assembly of gas-filled chambers or beads 13, into a biocompatible elastomeric shell 11. The diphasic portion; that is, the gas-filled beads, may be introduced within the shell 11 either prior to filling the shell with fluid or after the shell has been fluid-filled. As will be discussed later, the diphasic portion may also be introduced into a fluid-filled prosthesis to displace a portion of the fluid even following implantation. This is useful for reducing the density of a previously implanted prosthesis in situ.

As used herein, the term "beads" or "bead" refers to a gas-filled chamber, the walls of which may be elongate, spherical, cylindrical or any shape that is convenient to manufacture. In a preferred embodiment the two phase (biphasic) component of the triphasic filler 12 is a string of extruded gas-filled elastomeric beads 13 with extrudate 14 therebetween forming a flexible connection wherein each bead is free of gaseous communication with any other bead. The elastomer is preferably cured silicone rubber, but any biocompatible elastomer which is impervious to the liquid phase may be used. The exact size of the extruded beads or the tubing from which they are formed may be empirically determined by considering the overall desired density reduction of the prosthesis as well as the esthetics or the final "feel" of the prosthesis. The important factor is that the density of the prostheses, as a whole, be comparable to or less than the density of the surrounding tissue. It is also preferred that, within the limitations imposed by the discrete structure of the diphasic portion of the filler, the density of the prothesis be substantially homogeneous throughout its volume. Preferably, the chains of gas-filled beads are interlinked to prevent the gas-filled beads or chambers from shifting or concentrating in a particular volume within the prosthesis. The range of the outer diameter of the beads is preferably less than 5 mm and more that ⅕th of a millimeter. The thickness of the wall of the bead may be arrived at empirically.

Figure 4:
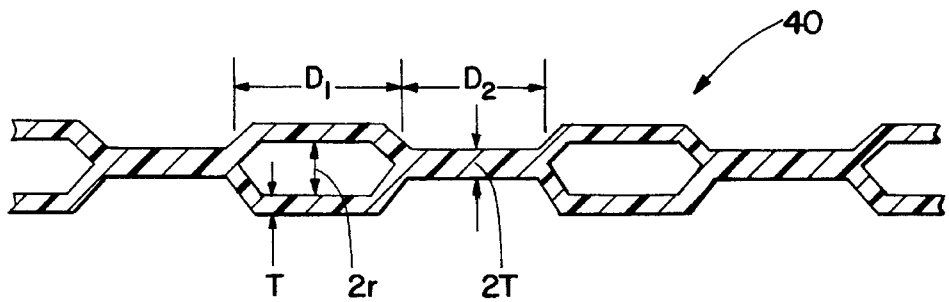
FIG. 4 is a cutaway longitudinal section of a segment of a chain of cylindrical gas-filled chambers.

Turning now to FIG. 4 a segment of the diphasic portion of the filler comprising a chain of interconnected gas filled chambers is shown. The segment 40 has two distinct repeating elements: a cylindrical gas-filled element having an inner radius r and a length $D_1$; and a silicone element connecting the gas-filled elements having a length $D_2$. Each element has a different density. For the convenience we can set the wall thickness T of the gas-filled element equal to one-half the diameter of the silicone element. Considering the two elements as a unit, the length of the unit is $$L_u = D_1 + D_2 \tag{1}$$

It can be shown that if $D_E$ is the effective density of a unit and $D_{sil}$=the density of the silicone portions of a unit ($\approx$1, 2), then $$D_E \approx \frac{D_{sil}}{1 + \frac{rD_1}{T^2(D_1 + D_2)}} \qquad (2)$$

The density $D_{sil}$ of Silastic® brand of silicone is $D_{sil}=1.2$ and the density of tissue is $D_{tis}\approx 0.93$. As seen from equation (2) the density $D_s$ of a unit of filler can be varied by either changing the ratio of $r_1$ to T or the length of the elements $D_1$ and $D_2$. If we arbitrarily set the length of the gas-filled segment $D_1=2D_2$, then $$D_E = \frac{D_{sil}}{1 + \left(\frac{r}{T}\right)^2 \left(\frac{2}{3}\right)} \qquad (3)$$

if $$\frac{r}{T} \approx \frac{3}{1} \qquad (4)$$

$$D_E = \frac{1.2}{1 + 9\left(\frac{2}{3}\right)} = \frac{1.2}{7} \approx 0.17 \qquad (5)$$

Therefore, the ratio of the radius of the gas-filled chamber r to the wall thickness T can be adjusted to effect the necessary density reduction in the 2-phase component of the filler. As will be discussed later, if the 2-phase component of the filler is extruded, this can be accomplished by adjusting the position and diameter of the mandril and the size of the die nozzle in the extruder head accordingly.

Figure 2:
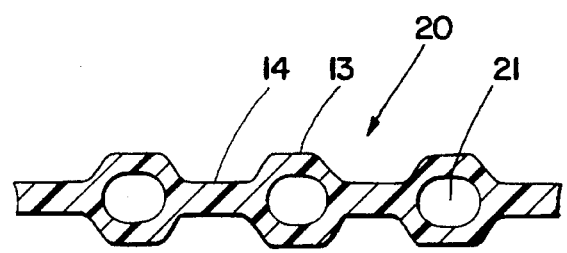
FIG. 2 is a cutaway longitudinal sectional view of a segment of the string of interconnected beads (gas-filled chambers) used as a filler in FIG. 1.
Figure 3:
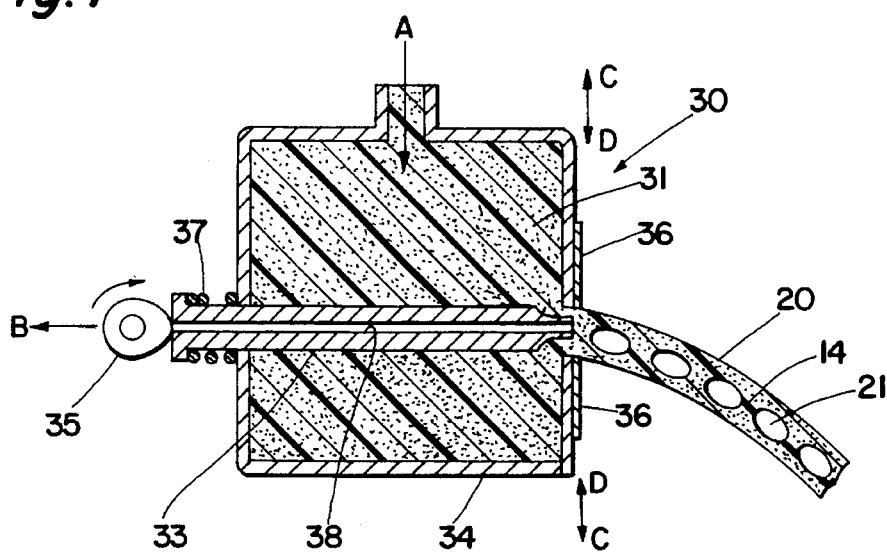
FIG. 3 is a schematic drawing of an extrusion apparatus for extruding the solid/gas phases of the prosthesis filler according to the present invention.

Silicone rubber is a preferred extrudable material for forming the chambers or beads. The central lumen of the extruded tubing which is constricted into beads during extrusion is preferably filled with nitrogen. As the tubing is being extruded it is compressed at intervals by constricting the size of the opening in the die nozzle to form essentially a string of gas-filled beads. The beads 13, which may resemble a string of sausages, have nitrogen gas 21 permanently trapped within the inner lumen. The string of gas-filled beads generally indicated at numeral 20 in FIG. 2 can conveniently be extruded in an apparatus as shown in FIG. 3. An extruder head 30 receives an elastomeric extrudate 31 from an extrudate reservoir (not shown). The extrudate 31 is forced through a die nozzle opening 32 to emerge from the extruder head 30 as a tube 20. If a mandril 33 is moved so that its tip partially blocks the die nozzle opening 32, the extrudate 31 is forced around the tip of the mandril 33 forming a gas-filled inner lumen 21 in the extruded tube 20. If the tip of the mandril 33 is then withdrawn (moved in the direction of arrow B) the lumen 21 will close. Thus, shuttling the tip of the mandril 33 in and out of the die nozzle opening 32 during extrusion will form gas filled pockets in the tubing. The gas is injected by suitable means through a bore 38 within the mandril. The injected gas is entrapped in the extrudate when the tip of the mandril is within the die nozzle opening. If slides 36 are moved in such as way as to partially close the die nozzle opening 32 as the mandril 33 is being withdrawn, the tubing "pinches" or is reduced in outer diameter as it exits the head. If the mandril 33 and the die nozzle opening slides 36 are adjusted to move synchronously, a chain of interconnected beads as shown in FIG. 2 will be extruded. As this tubing is extruded and formed into the biphasic portion of the prosthesis filler, the chain may be directed onto a moving platform (not shown). The motion of the platform may be adjusted to facilitate the contouring of the accumulating pile of interlinked gas-filled beads with entrapped nitrogen gas. The pile may be conical in shape, having the appearance of a rope being unwound as it falls onto the ground, or it may be compressed or molded to conform to a particular desirable shape then vulcanized. Overall, the form of the biphasic portion of the prosthesis filler is an interlinked mass of beads with trapped gas within the beads. As stated above, raw unvulcanized silicone elastomer is the extrudable material of choice for forming the beads. The chain of sausage-like beads may be readily interlinked after forming by vulcanizing the formed biphasic portion of the filler at elevated temperature. The walls of adjacent beads will stick together. Alternatively, the chain of beads can be partially coated with a silicone dispersion that vulcanizes at room temperature and loosely compressed into the shell. The dispersion will cure leaving a biphasic filler that will be elastically cohesive while, at the same time, compressible. Where deformation is desirable, outer wall adhesions need not be formed and the biphasic filler will exhibit a degree of deformation "flow".

After forming the extruded chain into the desired shape which will depend on the design of the prosthesis the chains are interlinked. This interlinking mass of small beads with entrapped nitrogen is then placed within an elastomeric shell that has been previously formed by dip casting on a mandril. The whole cavity of the shell may then be filled with normal saline, dextran or other bio-compatible liquids. It is possible that hyaluronic acid or hydrogels may provide additional antifriction effects that will give the fluid filled prosthesis a more desirable feel. The outer surface of the shell may also be textured to permit tissue ingrowth to promote stabilization of the device and diffusion of the viscoelastic interface discussed in the previous section. The nitrogen gas trapped within Silastic® tubing produces significant density reduction of the prosthesis, the interlinked tubing adds significantly to the structural integrity of the implant, and the gas phase within the tubing offers a slight compressibility to the device further ameliorating the contractile forces occurring during capsule formation. All these advantages can be obtained at the time of device manufacture.

Figure 5:
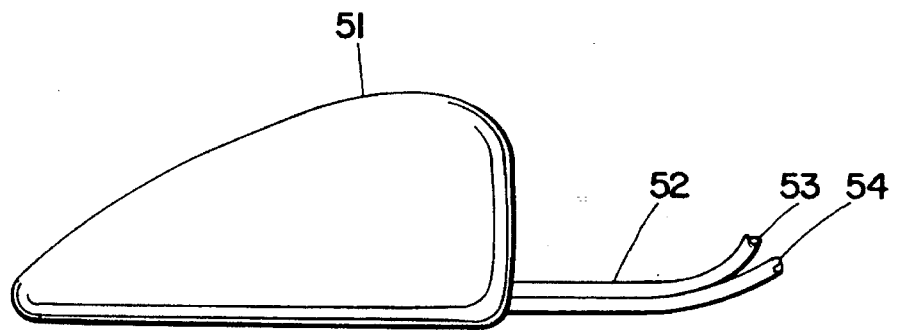
FIG. 5 shows a perspective view of a breast implant having remotely accessible dual channels in fluid communication with the interior chamber of the implant.
Figure 6:
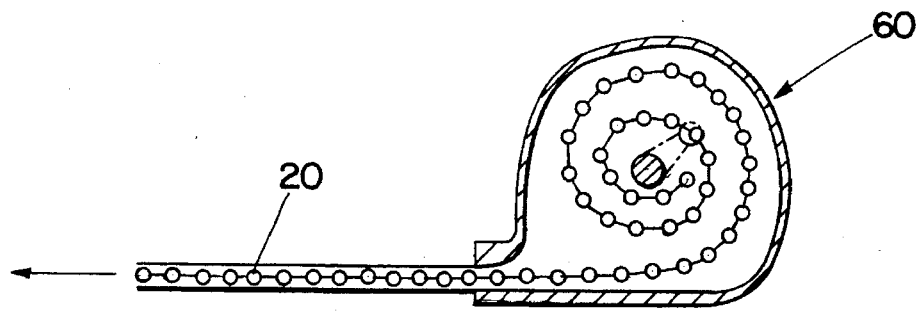
FIG. 6 is a sectional view of a filler injector.
Figure 7:
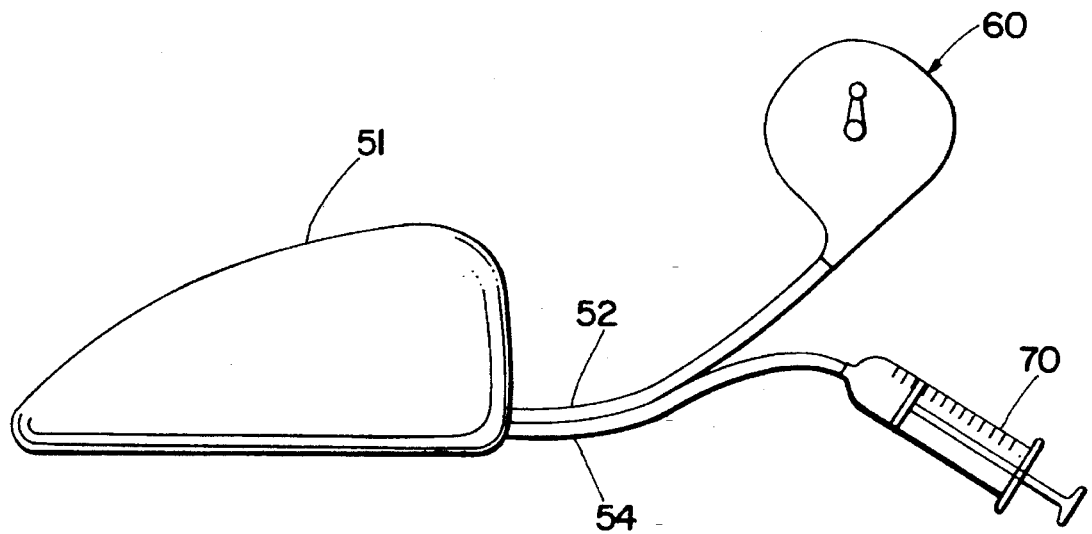
FIG. 7 is a schematic representation showing the use of dual channels to inject the two phase (diphasic) component of a filler into a prosthesis while displacing a portion of the fluid component from within the implant.

The novel diphasic component of the filler described herein may be injected into an endoscopically implanted prosthesis as shown in FIGS. 5–7. Following endoscopic surgical insertion (not shown) of a collapsible shell 51, the shell is filled with saline through a fill port on the surface of the shell in the manner well known in the art. After filling with saline, the diphasic component of the filler (not shown in FIG. 5) can be serially introduced via a secondary lumen 53 into the prosthesis by means of an injector 60 shown in FIG. 6. The injection of the diphasic component will specifically displace a measured volume of saline, provide a desired density and weight reduction and add to structural integrity of the device. FIG. 7 shows a schematic representation of a suitable System for such endoscopic (minimal incision) insertion of filler.

The above-described embodiment of an implantable prosthesis made in accordance with the present invention offers numerous advantages. The filler provides a controllable density reduction to closely match the density of surrounding tissue by use of a combination of extruded elastomer, entrapped nitrogen and a fluid filler such as saline in the remaining space. Because of the interlinking internal structure, the filler will retain its shape, even in the event of shell rupture without causing a collapse of the whole prosthesis. In the event of shell rupture the prosthesis will retain approximately 80% of its size and shape. There are no elements of unknown toxicity that may bleed into surrounding tissue and cause clinical problems. The beads need not be interlinked because in the event of rupture the relatively large beads would be retained by the capsule surrounding the prosthesis and, being too large for ingestion and active transport by macrophages, effectively trapped within the capsular boundary. The only material that would bleed or otherwise leave the prosthesis in case of a rupture is the liquid phase such as normal saline which is readily absorbed by tissue and excreted. Another advantage of this design is significant density reduction and improved viscoelastic coupling between the surrounding tissue and the device. Since the device contains a filler material having a density that is less than or equal to the density of the surrounding tissue, it causes less injury at the prosthesis/tissue interface when in motion. An additional factor to consider is that because of the presence of the gas phase within the prosthesis itself the prosthesis may be compressed. Even if early capsule formation does occur during the early post surgical period, the device would be able to allow for some compressibility and thereby yield give way to the initial biological contracture. This in itself may offer some advantages on the final deformation effects that occur with current non-compressible implants.

In conclusion, this invention describes both the design and the manufacturing process for a bio-compatible breast implant device utilizing currently established, medically safe materials, achieving structural integrity, density reduction and compressibility. Through these factors, this device achieves significant improvement over the existing technology. Other embodiments include sticky or self-adhering closed-cell biocompatible particles as the solid/gaseous phase is that its density may be adjusted to accommodate a variety of liquid fillers to produce a triphasic filling material and gaining significant advantages in function and patient safety over current existing designs. As stated earlier, the gas-filled chambers or beads used in the filler need not be interconnected if they are dimensioned to prevent ingestion by macrophage in the case of rupture of the prosthesis shell.

The gas-filled chambers or beads, whether free or interconnected, may be coated with a lubricious material such as a hydrogel to provide a more natural feel to such a prosthesis. It should be understood that the incorporation of gas-filled chambers within a fluid-filled medical implant is a means for reducing the density of the prosthesis filler to more closely approximate that of the surrounding soft tissue. The reduction in density reduces the relative motion and microtrauma between the prosthesis and the surrounding capsule-associated tissue and/or between the capsule-associated tissue and surrounding soft tissue. While gas-filled beads are presented as a means for reducing the density of a fluid-filled medical implant, any fluid-filled implant having a density less than or equal to the density of the surrounding soft tissue will reduce the incidence of motion-induced interfacial microtrauma and subsequent capsular contracture.

What I claim is:

1. A prosthesis for implantation beneath the skin of a patient thereafter to be surrounded by tissue, said prosthesis comprising:

(a) an elastomeric outer shell; and (b) a filler enclosed by said elastomeric outer shell and wherein said filler further comprises, in combination, a fluid and a string comprising a plurality of interconnected beads, each bead of said plurality of interconnected beads comprising a gas filled chamber and wherein each said bead is free of gaseous communication with any other said bead.

2. The prosthesis of claim 1 wherein said filler has a density which is less than or equal to the density of said tissue.

* * * * *